United States Patent [19]
Flanagan

[11] Patent Number: 5,872,357
[45] Date of Patent: Feb. 16, 1999

[54] MASS SPECTROMETRY CALIBRATION USING HOMOGENEOUSLY SUBSTITUTED FLUORINATED TRIAZATRIPHOSPHORINES

[75] Inventor: J. Michael Flanagan, Sunnyvale, Calif.

[73] Assignee: Hewlett-Packard Company, Palo Alto, Calif.

[21] Appl. No.: 866,724

[22] Filed: May 30, 1997

[51] Int. Cl.$^6$ .............................. B01D 59/44; H01J 49/00
[52] U.S. Cl. ....................... 250/252.1; 250/282
[58] Field of Search ................ 250/252.1, 282

[56] References Cited

U.S. PATENT DOCUMENTS

| | | | |
|---|---|---|---|
| 4,073,624 | 2/1978 | Huston et al. | 44/1 R |
| 4,260,886 | 4/1981 | Grilletto et al. | 250/288 |
| 4,687,929 | 8/1987 | Browner et al. | 250/282 |
| 4,847,493 | 7/1989 | Sodal et al. | 250/252.1 |
| 5,051,583 | 9/1991 | Mimura et al. | 250/288 |
| 5,401,664 | 3/1995 | Larson et al. | 436/173 |
| 5,545,895 | 8/1996 | Wright et al. | 250/252.1 |
| 5,600,134 | 2/1997 | Ashe et al. | 250/252.1 |
| 5,686,726 | 11/1997 | Fenn et al. | 250/282 |

OTHER PUBLICATIONS

Cody et al., "Electrospray Ionization/Magnetic Sector Mass Spectrometry: Calibration, Resolution, and Accurate Mass Measurements," *Anal. Chem.*, 64:1561–1570 (1992).

Heeremans et al., "Acetic Acid Cluster Ions for Tuning and Calibration in Thermospray Liquid Chromotography /Mass Spectrometry," *Organic Mass Spect.*, 24: 109–112 (1989).

Hewlett Packard/Bruker, "The Esquire–LC Ion Trap LC/MS$^{(n)}$ System," (Brochure), 1–12 (1997).

Ho et al., "Mass Transport and Calibration in Liquid Chromatography Particle Beam Mass Spectrometry," *J. Am. Soc. Mass Spectr.*, 3:662–671 (1992).

Moini "Ultramark 1621 as a Calibration/Reference Compound for Mass Spectrometry. II. Positive– and Negative–Ion Electrospray Ionization," *Rapid Communications in Mass Spectrometry*, 8:711–714 (1994).

Saar et al., "Improved Tuning and Calibration in Liquid Chromatography/Thermospray Mass Spectrometry Using Acetic Acid Cluster Ions," *Organic Mass Spectrometry*, 26:660–663 (1991).

Stout et al., "Tuning and Calibration in Thermospray Liquid Chromatography/Mass Spectrometry Using Trifluoroacetic Acid Cluster Ions," *Anal. Chem.*, 61:2126–2128 (1989).

Stout et al., "Tuning and Calibration in Thermospray Liquid Chromatography/Mass Spectrometry Using Perfluorinated Alkyl Acids and Their Ammonium Salts," *Organic Mass Spectrometry*, 25:187–190 (1990).

*Primary Examiner*—Bruce Anderson

[57] ABSTRACT

Calibrant compositions are provided for use in either electrospray or APCI mass spectrometry, and can be used in either positive-ionization or negative-ionization modes. The compositions contain a primary calibrant preferably comprised of a mixture of homogeneously substituted triazatriphosphorines, and a secondary calibrant enabling calibration at relatively low mass-to-charge (m/z) values. The compositions enable calibration across a broad mass spectral range. Novel triazatriphosphorine compounds are provided as well, as are methods for calibrating mass spectrometers using the novel calibrant compositions.

32 Claims, 9 Drawing Sheets

MASS SPECTROMETRY CALIBRATION USING HOMOGENEOUSLY SUBSTITUTED FLUORINATED TRIAZATRIPHOSPHORINES

TECHNICAL FIELD

The present invention relates generally to calibration of mass spectrometers. More particularly, the invention relates to novel methods and compositions for calibrating mass spectrometers operating in electrospray (ES) and atmospheric pressure chemical ionization (APCI) modes. The invention additionally relates to novel compounds useful in the calibrant compositions disclosed and claimed herein.

BACKGROUND

Many methods and compositions are known for calibrating mass spectrometers. As explained by Moini in *Rapid Communications in Mass Spectrometry* 8:711–714(1994), use of calibration compounds which generate highly accurate mass reference peaks is critically important in mass spectrometry, insofar as any error introduced by a calibrant can be magnified and cause a significant loss in accuracy.

The compounds and compositions used to calibrate mass spectrometers vary widely. Many of the known calibrating compositions have a number of limitations. For example, most calibrants are useful in calibrating only certain ranges of a mass spectrum but are not useful across a broad range of mass-to-charge (m/z) values. Many calibrants are useful in electrospray mass spectrometry but cannot be used in APCI mass spectrometry and vice versa, or may be limited to use in only one ion polarity. Furthermore, some calibrants may include significant isotopic contributions (i.e., $^{13}C$) with increasing mass-to-charge or may be multiply charged limiting their effectiveness as reference masses. Additional shortcomings may include rapid ion source contamination, loss of sensitivity, or a combination of factors.

Several references are of interest insofar as they pertain to calibration compounds and/or methods for use in mass spectrometry. U.S. Pat. No. 4,260,886 to Grilletto et al., for example, describes a method for improving the accuracy of a spectrometric measurement of a small volume of gas by carefully monitoring the volume and injection rate of the calibrating gas. U.S. Pat. No. 5,401,664 to Larson et al. describes a ratiometric calibration method for determining the concentration of dibutyl and monobutyl phosphate degradation products resulting from a solvent extraction process, the method involving the use of a labeled internal standard comprising the deuterated phosphates of interest and bistrimethylsilyltrifluoracetamide as a silylating agent. U.S. Pat. No. 4,847,493 to Sodal et al. describes a calibration assembly for use in calibrating a mass spectrometer and designed to reduce the amount of calibration gas and time that is used in the calibration process. U.S. Pat. No. 5,051,583 to Mimura et al. describes an atmospheric pressure ionization type mass spectrometer in which a mass marker of the mass spectrometer is derived using water cluster ions accelerated by a drift voltage applied between the ionization chamber of the spectrometer and the spectrometer's mass analysis region.

Additional references of interest are Stout et al., *Organic Mass Spectrometry* 25:187–190 (1990), Saar et al., *Organic Mass Spectrometry* 26:660–663 (1991), and Stout et al., *Anal. Chem.* 61:2126–2128 (1989), which relate to tuning and calibration in thermospray liquid chromatography/mass spectrometer systems using perfluorinated alkyl acids, ammonium salts of perfluorinated alkyl acids (Stout et al. (1990)), acetic acid cluster ions (Saar et al.), and trifluoroacetic acid cluster ions (Stout et al. (1989)). Moini, supra, describes the use of "Ultramark® 1621" as a calibration/reference compound in electrospray mass spectrometry. Ultramark® 1621 (available from PCR, Gainesville, Fla.) is a mixture of fluorinated phosphazines, with each phosphazine randomly and heterogeneously substituted, i.e., the various substituents bound to the phosphorus atoms in the heterocyclic phosphazine ring are each different (note that the compounds referred to in Moini as "phosphazines" are referred to herein as "triazatriphosphorines"). While the mixture is somewhat effective, the Moini mixture is useful only in the mass range of approximately m/z 900 to m/z 2100; the mixture is not useful across a broad range of m/z values. The mass spectra obtained with the Moini heterogeneous mixture are characterized by a Gaussian distribution of mass peaks approximately 100 amu apart, a distribution which is in general undesirable since the "low end" and "high end" ions are significantly less intense than those which are mid-spectrum. Finally, the mixture described by Moini calls for a relatively high concentration of Ultramark® 1621 (0.05%) which can result in increased background signal (i.e., memory effects).

The present invention addresses each of these limitations in the prior art by providing a calibrant composition which is useful across a broad spectral range, can be used in both electrospray mass spectrometry and in APCI mass spectrometry, and is useful in both positive-ionization and negative-ionization modes. The composition utilizes singly charged compounds which provide for more accurate mass measurements, not just with singly charged species but with multiply charged species (e.g., proteins) as well. The compounds are highly sensitive, nontoxic, non-odorous, relatively low cost, and stable in solution at room temperature for on the order of a year or more.

SUMMARY OF THE INVENTION

Accordingly, it is a primary object of the present invention to provide a novel calibrant composition useful across a broad spectral range.

It is a further object of the present invention to provide a novel calibrant composition useful in electrospray mass spectrometry.

It is still a further object of the present invention to provide a novel calibrant composition useful in APCI mass spectrometry.

It is yet a further object of the present invention to provide a novel calibrant composition which is useful in conjunction with both positive-ionization and negative-ionization modes of mass spectrometric operation.

It is another object of the invention to provide a method for calibrating a mass spectrometer using the compounds and compositions of the invention.

It is still another object of the invention to provide novel triazatriphosphorine compounds useful as mass spectrometer calibrants.

Additional objects, advantages and novel features of the invention will be set forth in part in the description which follows, and in part will become apparent to those skilled in the art upon examination of the following, or may be learned by practice of the invention.

In one aspect, then, the invention relates to a calibrant composition for use in mass spectrometry. The composition contains a primary calibrant comprised of a homogeneously substituted triazatriphosphorine compound, and a secondary calibrant comprised of a compound which enables calibration at a very low m/z, typically below 150, and more preferably below 120. The composition also contains a solvent, generally a common HPLC solvent such as a mixture of acetonitrile and water, which is present in an amount effective to dissolve all components of the composition. When used in conjunction with electrospray mass spectrometry, the calibrant composition additionally contains a triazine compound.

In another aspect of the invention, an improved method is provided for calibrating a mass spectrometer using the calibrant compositions of the invention. In general, the method involves obtaining real-time mass spectra of the calibrant composition of the invention, and conducting comparisons of the m/z values of the mass peaks obtained with the known (theoretical) masses for the individual components in the composition. Based on the comparisons, the mass spectrometer device is internally adjusted to compensate for the differences noted. This calibration process ensures that mass spectra of samples containing unknown components are accurate.

In still another aspect of the invention, a number of novel compounds are provided which are useful as the primary calibrants herein. The novel compounds are homogeneously substituted triazatriphosphorines as will be described in detail hereinbelow.

DETAILED DESCRIPTION OF THE INVENTION

Before the invention is described in detail, it is to be understood that this invention is not limited to specific compound mixtures or calibration techniques as such may vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

In this specification and in the claims which follow, reference will be made to a number of terms which shall be defined to have the following meanings:

A "triazatriphosphorine" as used herein is a compound having the structural formula The triazatriphosphorines used in the calibrant compositions of the invention are substituted so that each of the phosphorus atoms in the heterocyclic ring bears two substituents.

The term "homogeneously substituted triazatriphosphorine," as used herein to refer to the substituted triazatriphosphorines which serve as the primary calibrants, is intended to mean that there are six identical substituents bound to the heterocyclic ring, with two substituents on each phosphorus atom.

The term "amphoteric" is used herein in its conventional sense to refer to a compound which bears both a positive and a negative charge, or to a compound which by modifying the pH of its environment is capable of bearing both a positive and a negative charge.

The term "nitrogen-containing heterocycle" is used to refer to heterocyclic compounds of one or two five- or six-membered rings containing one to three nitrogen atoms per ring. Examples of suitable nitrogen-containing heterocycles include, but are not limited to, pyridine, pyrimidine, pyrazine, pyrazole, pyrazoline, pyridazine, purine, pyrrolidine, pyrrole, piperidine, morpholine, quinoline, indole, imidazole, benzimidazole, and 1,2,4-triazole.

The calibrant compositions of the invention contain predetermined concentrations of (1) a primary calibrant comprised of a homogeneously substituted triazatriphosphorine compound and (2) a secondary calibrant comprised of a compound selected to enable calibration at an m/z below approximately 150, in a solvent effective to dissolve both calibrants and any other components that may be present in the composition. The primary and secondary calibrants are such that they can be used in either positive-ionization or negative-ionization modes, or both, and in either electrospray mass spectrometry, APCI mass spectrometry, or both. As will be discussed further below, certain calibrants are preferred for use in positive-ionization operation, while others are preferred for use in negative-ionization operation; similarly, certain calibrants are preferred for use in electrospray mass spectrometry while others are preferred for use in conjunction with APCI mass spectrometry.

The primary calibrant is comprised of a triazatriphosphorine in which each phosphorus atom of the heterocyclic ring is bound to two substituents, and wherein the six substituents on the heterocyclic ring are identical. Preferred compounds within this group are represented by the structural formula (I)

wherein $R_f$ is —$OCH_3$, —O—$(CF_2)_{n'}$—$CF_2H$, —O—$(CH_2)_m$—$(CF_2)_n$—$CF_2R$ or —O—$(CH_2)_m$—$(CF_2)_{n-1}$—CHF—$CF_2R$ in which m is 0, 1 or 2, n' is an integer in the range of 0 to 16 inclusive, n is an integer in the range of 1 to 16 inclusive, R is hydrogen or fluoro, and each of the $R_f$ substituents is identical to the others. More preferred compounds within this group are wherein $R_f$ is —$OCH_3$ or —O—$CH_2$—$(CF_2)_n$—$CF_2H$ (i.e., —O—(CH$_2$)$_m$—(CF$_2$)$_n$—CF$_2$R wherein m is 1 R is hydrogen) in which n is in the range of 1 to 12, more preferably in the range of 1 to 8. More preferred compounds also include —O—(CF$_2$)$_{n'}$—CF$_2$H in which n' is in the range of 0 to 9. Generally, compounds with larger R$_f$ substituents, i.e., wherein n is larger, will broaden the mass calibration range by enabling calibration at a higher m/z. However, such compounds may require an alteration in the quantity or type of solvent used.

In order to provide for calibration across an extended mass range, it is preferred that the primary calibrant comprise a mixture of different triazatriphosphorine compounds, with each compound having the general structure of formula (I) and selected to enable calibration across a breadth of m/z values. Optimally, between about five and eight compounds are used.

Specific such compounds include, but are not limited to, the following.

R$_f$=—OCH$_3$
2,2,4,4,6,6-hexahydro-2,2,4,4,6,6-hexamethoxy-1,3,5,2,4, 6-triazatriphosphorine (CAS #957-13-1; also sometimes referred to herein as HP-0321).

R$_f$=—O—CH$_2$—(CF$_2$)$_n$—CF$_2$H
R$_f$=—O—CH$_2$—CF$_2$H:
2,4,4,6,6-hexakis(2,2-difluoroethoxy)-2,2,4,4,6,6-hexahydro-1,3,5,2,4,6-triazatriphosphorine (CAS #186817-57-2; also sometimes referred to herein as HP-0621).

R$_f$=—O—CH$_2$—CF$_2$—CF$_2$H:
2,2,4,4,6,6-hexahydro-2,2,4,4,6,6-hexakis((2,2,3,3-tetrafluoropropyl)oxy)-1,3,5,2,4,6-triazatriphosphorine (CAS #58943-98-9; also sometimes referred to herein as HP-0921).

R$_f$=—O—CH$_2$—(CF$_2$)$_2$—CF$_2$H:
2,2,4,4,6,6-hexakis((2,2,3,3,4,4-hexafluorobutyl)oxy)-2,2, 4,4,6,6-hexahydro-1,3,5,2,4,6-triazatriphosphorine (CAS #186406-47-3; also sometimes referred to herein as HP-1221).

R$_f$=—O—CH$_2$—(CF$_2$)$_3$—CF$_2$H:
2,2,4,4,6,6-hexahydro-2,2,4,4,6,6-hexakis((2,2,3,3,4,4,5,5-octafluoropentyl)oxy)-1,3,5,2,4,6-triazatriphosphorine (CAS #16059-16-8; also sometimes referred to herein as HP-1521).

R$_f$=—O—CH$_2$—(CF$_2$)$_4$—CF$_2$H:
2,2,4,4,6,6-hexakis((2,2,3,3,4,4,5,5,6,6-decafluorohexyl)oxy)-2,2,4,4,6,6-hexahydro-1,3,5,2,4,6-triazatriphosphorine (CAS #186406-48-4; also sometimes referred to herein as HP-1821).

R$_f$=—O—CH$_2$—(CF$_2$)$_5$—CF$_2$H:
2,2,4,4,6,6-hexahydro-2,2,4,4,6,6-hexakis((2,2,3,3,4,4,5,5, 6,6,7,7-dodecafluoro-heptyl) oxy)-1,3,5,2,4,6-triazatriphosphorine (CAS #3830-74-8; also sometimes referred to herein as HP-2121).

R$_f$=—O—CH$_2$—(CF$_2$)$_6$—CF$_2$H:
2,2,4,4,6,6-hexahydro-2,2,4,4,6,6-hexakis((2,2,3,3,4,4,5,5, 6,6,7,7,8,8-tetradecafluorooctyl)oxy)-1,3,5,2,4,6-triazatriphosphorine (CAS #186406-49-5; also sometimes referred to herein as HP-2421).

R$_f$=—O—CH$_2$—(CF$_2$)$_7$—CF$_2$H:
2,2,4,4,6,6-hexahydro-2,2,4,4,6,6-hexakis((2,2,3,3,4,4,5,5, 6,6,7,7,8,8,9,9-hexadecafluorononyl)oxy)-1,3,5,2,4,6-triazatriphosphorine (CAS #186043-67-4; also sometimes referred to herein as HP-2721).

R$_f$=—O—CH$_2$—(CF$_2$)$_8$—CF$_2$H:
2,2,4,4,6,6-hexahydro-2,2,4,4,6,6-hexakis((2,2,3,3,4,4,5,5, 6,6,7,7,8,8,9,9,10,10-octadecafluorodecyl)oxy)-1,3,5,2,4, 6-triazatriphosphorine (CAS #186406-50-8; also sometimes referred to herein as HP-3021).

R$_f$=—O—CH$_2$—CF$_2$—CFH—CF$_3$
2,2,4,4,6,6-hexakis((2,2,3,4,4,4-hexafluorobutyl)oxy)-2,2, 4,4,6,6-hexahydro-1,3,5,2,4,6-triazatriphosphorine.

R$_f$=—O—CH$_2$—(CF$_2$)$_n$CF$_3$
R$_f$=—O—CH$_2$—CF$_2$—CF$_3$:
2,2,4,4,6,6-hexahydro-2,2,4,4,6,6-hexakis((2,2,3,3,3-pentafluoropropyl)oxy)-1,3,5,2,4,6-triazatriphosphorine (CAS #429-18-5; also sometimes referred to herein as HP-1029).

R$_f$=—O—CH$_2$—(CF$_2$)$_2$—CF$_3$:
2,2,4,4,6,6-hexahydro-2,2,4,4,6,6-hexakis((2,2,3,3,4,4,4-heptafluorobutyl)oxy)-1,3,5,2,4,6-triazatriphosphorine.

R$_f$=—O—CH$_2$—(CF$_2$)$_4$—CF$_3$:
2,2,4,4,6,6-hexahydro-2,2,4,4,6,6-hexakis((2,2,3,3,4,4,5,5, 6,6,6-undecafluorohexyl)oxy)-1,3,5,2,4,6-triazatriphosphorine.

R$_f$=—O—CH$_2$—(CF$_2$)$_6$—CF$_3$:
2,2,4,4,6,6-hexahydro-2,2,4,4,6,6-hexakis((2,2,3,3,4,4,5,5, 6,6,7,7,8,8,8-pentadecafluorooctyl)oxy)-1,3,5,2,4,6-triazatriphosphorine (CAS #186406-49-5; also sometimes referred to herein as HP-2529).

R$_f$=—O—CH$_2$—(CF$_2$)$_8$—CF$_3$:
2,2,4,4,6,6-hexahydro-2,2,4,4,6,6-hexakis((2,2,3,3,4,4,5,5, 6,6,7,7,8,8,9,9,10,10,10-nonadecafluorodecyl)oxy)-1,3,5, 2,4,6-triazatriphosphorine (also sometimes referred to herein as HP-3129).

Within the aforementioned list of compounds, as noted above, those that are particularly preferred have R$_f$=—OCH$_3$ (HP-0321) or R$_f$=—O—CH$_2$—(CF$_2$)$_n$—CF$_2$H, and, of these, those that are most preferred have R$_f$=—OCH$_3$ or R$_f$=—O—CH$_2$—(CF$_2$)$_n$—CF$_2$H wherein n is 0 (HP-0621), 1 (HP-0921), 3 (HP-1521), 5 (HP-2121), or 7 (HP-2721).

For the preferred compositions of the invention, in which the primary calibrant comprises five to eight different fluorinated triazatriphosphorines each having the structure of formula (I), the concentration of each triazaphosphorine component in the composition is generally in the range of about 0.1 to 30 µM, preferably in the range of about 0.5 to 25 µM, and most preferably in the range of about 0.5 to 20 µM. With more sensitive compounds, such as the hexamethoxy-substituted triazatriphosphorine, lower concentrations can be used (on the order of 0.5 to 5 µM).

Each substituted triazatriphosphorine which can serve as a primary calibrant may be synthesized using conventional techniques known to those skilled in the art of synthetic organic chemistry or as described in the pertinent literature (alternatively, the compounds may be obtained commercially, from SynQuest Laboratories, Alachua, Fla.). The schemes shown in FIGS. 1 through 4 illustrate possible modes of preparing the substituted triazatriphosphorines useful herein. As may be seen, generally it is the fluorinated alcohols which are prepared first, represented as R$_f$OH in the figures, which are then caused to react with a hexachloro-substituted triazatriphosphorine as may be obtained commercially. Again, it should be emphasized that variations on the synthetic methods used are possible, as are alternative synthetic techniques.

The secondary calibrant is one that is effective to provide low mass calibration, i.e., at m/z values below about 150 and preferably below about 120. The compound may be, for example, betaine or purine, or a nitrogen-containing heterocycle. The nitrogen-containing heterocyclic is preferably amphoteric in that it is substituted with a group which is ionizable to give an anionic moiety, e.g., a hydroxyl or carboxyl substituent, preferably a hydroxyl substituent. Exemplary such compounds include purine, 2-hydroxypyridine, 3-hydroxypyridine, 3-hydroxy-2-methylpyridine and picolinic acid. For calibration in electrospray mass spectrometry conducted in the positive-ionization mode, betaine is a preferred secondary calibrant; with APCI mass spectrometry, purine, 3-hydroxy-2-methylpyridine, 2-hydroxypyridine and 3-hydroxypyridine are preferred. The concentration of the secondary calibrant is generally in the range of approximately 10 to 50 μM.

For electrospray mass spectrometry, the calibrant composition contains a third calibrant comprised of a fluorinated triazine, i.e., a compound having the structural formula (II)

(II)

wherein each R' is —$(CF_2)_pCF_3$ wherein p is an integer in the range of 1 to 8 inclusive. One example of such a compound is tris(heptafluoropropyl)-1,3,5-triazine. Such compounds can be readily synthesized using known techniques, or may be obtained commercially, e.g., from PCR, Inc. (Gainesville, Fla.).

When used for electrospray mass spectrometry, it is also desirable that the composition contain a $C_2$–$C_{18}$, more typically $C_2$–$C_{10}$, fluorinated acid or salt thereof, preferably an inorganic salt. It is preferred that the acid is in salt form; examples of such compounds include the ammonium salt of trifluoroacetic acid (TFA$^-$NH$_4^+$) or the ammonium salt of perfluorinated octanoic acid, with the former compound representing a particularly preferred additive. Such acids and acid salts have been found to be extremely effective in adduct formation and enable use of the present compositions in both positive-ionization and negative-ionization modes of mass spectrometry. That is, adding a compound such as TFA$^-$NH$_4^+$ to the inventive calibrant compositions allows the compositions to be used in negative-ionization operation as well as positive-ionization operation. This is demonstrated in the examples herein. Generally, the acid or acid salt will be present at concentrations less than about 2 mM, typically at concentrations on the order of 1–2 mM.

Any number of solvents can be used in the calibrant composition, so long as the selected solvent or solvent mixture is effective to dissolve the primary and secondary calibrants and any other components which may be present in the mixture. Generally, any common HPLC solvent can be used, e.g., acetonitrile, isopropyl alcohol or the like. A particularly preferred solvent for both electrospray mass spectrometry and APCI mass spectrometry is a mixture containing primarily acetonitrile and water, with water preferably representing approximately 5% of the composition, by volume, and serving to dissolve the acid or acid salt, if present.

Relatively low viscosity solvent mixtures such as 80–95% acetonitrile calibrant solutions are particularly amenable to dispensation by an automated liquid calibrant delivery system. In the present APCI calibrant composition, 0.5 to 1% chloroform is preferably added as a charge carrier for negative mode APCI operation. Alternatively 5–10% oxygen if present in the vicinity of the corona discharge will serve the same purpose.

In use, the calibrant compositions may be used as an internal reference standard in an electrospray or APCI mass spectrometer. However, it is preferred to use the present calibrant compositions to tune a mass spectrometer. "Tuning" generally involves optimizing the ion optic lens settings, adjusting mass peak resolution and calibrating the mass axis. Tuning can be carried out manually by the user or with an "autotone" (an automated software tuning algorithm). The calibrant compositions herein provide singly charged, highly accurate reference masses which are used in optimizing tune parameters, adjusting mass peak resolution and calibrating the mass axis. An accurate calibration will help to ensure that accurate mass spectra are obtained for samples containing unknown components.

The present invention also encompasses a number of novel compounds which can serve as primary calibrants herein. The novel compounds are represented by structural formula (Ia)

(Ia)

wherein the R'$_f$ within any one compound are identical, and are selected from the group consisting of: —$OCH_2(CF_2)_2CF_2H$; —$OCH_2(CF_2)_4CF_2H$; —$OCH_2(CF_2)_6CF_2H$; —$OCH_2(CF_2)_8CF_2H$; —$OCH_2(CF_2)_6CF_3$; —$OCH_2(CF_2)_8CF_3$; and —$OCH_2$—$CF_2$—$CFH$—$CF_3$. These compounds are referred to elsewhere herein as 2,2,4,4,6,6-hexakis((2,2,3,3,4,4—hexa fluorobutyl)oxy)-2,2,4,4,6,6-hexahydro-1,3,5,2,4,6-triazatriphosphorine (HP-1221), 2,2,4,4,6,6-hexakis((2,2,3,3,4,4,5,5,6,6-decafluorohexyl)oxy)-2,2,4,4,6,6-hexahydro-1,3,5,2,4,6-triazatri-phosphorine (HP-1821), 2,2,4,4,6,6-hexahydro-2,2,4,4,6,6-hexakis ((2,2,3,3,4,4,5,5,6,6,7,7,8,8-tetradecafluorooctyl)oxy)-1,3,5,2,4,6-triazatriphosphorine (HP-2421), 2,2,4,4,6,6-hexahydro-2,2,4,4,6,6-hexakis((2,2,3,3,4,4,5,5,6,6,7,7,8,8,9,9,10,10-octadeca-fluorodecyl)oxy)-1,3,5,2,4,6-triazatriphosphorine (HP-3021), 2,2,4,4,6,6-hexahydro-2,2,4,4,6,6-hexakis((2,2,3,3,4,4,5,5,6,6,7,7,8,8,8-pentadecafluorooctyl)oxy)-1,3,5,2,4,6-triazatriphosphorine (HP-2529), 2,2,4,4,6,6-hexahydro-2,2,4,4,6,6-hexakis ((2,2,3,3,4,4,5,5,6,6,7,7,8,8,9,9,10,10,10-nonadecafluorodecyl)oxy)-1,3,5,2,4,6-triazatriphosphorine (HP-3129), and 2,2,4,4,6,6-hexakis((2,2,3,3,4,4,4-hexafluorobutyl)oxy)-2,2,4,4,6,6-hexahydro-1,3,5,2,4,6-triazatriphosphorine.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, journal articles and other references cited herein are incorporated by reference in their entireties.

The following examples are put forth so as to provide those of ordinary skill in the art with a complete disclosure and description of how to use the method of the invention, and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

Experimental

Electrospray and APCI mass spectra were obtained on an HP 1100 series LC-MSD, Product Number G1946A (Hewlett-Packard Co., Palo Alto, Calif.) with API-ES (Product Number G1948A) and APCI (Product Number G1947A) accessories.

ES spray chamber parameters: nebulizing gas ($N_2$), 20 psig; drying gas temperature, 300° C.; drying gas flow, 4.0 L/min.

APCI spray chamber parameters: nebulizing gas ($N_2$), 20 psig; drying gas temperature, 300° C.; drying gas flow, 3.0 L/min; and vaporizer temperature, 350° C.

Liquid calibrant flow rate was approximately 100 μl/min for both API-ES and APCI.

Additional experimental parameters are summarized in the following table:

TABLE 1

| Mode | Polarity | Vcap | Icor | Fragmentor | Skim2 | Lens1 | Lens2 | Iris |
|---|---|---|---|---|---|---|---|---|
| ES | Positive | 4000 | N/A | ramped | 8.0 | 1.6 | 36 | 350 |
| ES | Negative | 4000 | N/A | ramped | 8.0 | −3.3 | 38 | 65 |
| APCI | Positive | 4000 | 4 μA | ramped | 8.0 | 1.6 | 36 | 350 |
| APCI | Negative | 4000 | 4 μA | ramped | 8.0 | −3.3 | 38 | 6 |

All values are in volts, unless indicated otherwise.
Ion energy = 5 V, EM = 1711 V, HED = 10 kv
Abbreviations:
Vcap = capillary voltage
Icor = corona current
Quadrupole temperature = 100° C.
APCI scan range m/z 50–2150
ES scan range m/z 50–3000
Scan rate: (samples = 8, Averages = 1) = nominal 500 amu/sec

EXAMPLE 1

A composition for use in electrospray mass spectrometry calibration was prepared containing the components set forth in Table 1. In the table, the abbreviations are as follows: TFA, trifluoroacetic acid; ACN, acetonitrile; HP-0117, betaine; HP-0321, 2,2,4,4,6,6-hexahydro-2,2,4,4,6,6-hexamethoxy-1,3,5,2,4,6-triazatriphosphorine (CAS #957-13-1); HP-0585, tris(heptafluoropropyl)-1,3,5-triazine (CAS #915-76-4); HP-2,2,4,4,6,6-hexakis(2,2-difluoroethoxy)-2,2,4,4,6,6-hexahydro-1,3,5,2,4,6-triazatriphosphorine (CAS #186817-57-2); HP-0921, 2,2,4,4,6,6-hexahydro-2,2,4,4,6,6-hexakis ((2,2,3,3-tetrafluoropropyl)oxy)-1,3,5,2,4,6-triazatriphosphorine (CAS #58943-98-9); HP-1521, 2,2,4,4,6,6-hexahydro-2,2,4,4,6,6-hexakis((2,2,3,3,4,4,5,5-octafluoropentyl)oxy)-1,3,5,2,4,6-triazatriphosphorine (CAS #16059-16-8); HP-2121, 2,2,4,4,6,6-hexahydro-2,2,4,4,6,6-hexakis((2,2,3,3,4,4,5,5,6,6,7,7-dodecafluoroheptyl)oxy)-1,3,5,2,4,6-triazatriphosphorine (CAS #3830-74-8); HP-2721, 2,2,4,4,6,6-hexahydro- 2,2,4,4,6,6-hexakis((2,2,3,3,4,4,5,5,6,6,7,7,8,8,9,9-hexadecafluorononyl)oxy)-1,3,5,2,4,6-triazatriphosphorine (CAS #186043-67-4). The triazatriphosphorines were obtained from SynQuest Laboratories, Inc. (Alachua, Fla.); betaine was obtained from Sigma (St. Louis, Mo.); and the ammonium salt of trifluoroacetic acid was obtained from Aldrich (Milwaukee, Wis.).

In Table 2, the components of one liter of calibrant composition are set forth. The composition was prepared volumetrically; however, for larger batches, it is preferred that the composition be prepared gravimetrically. Calibrant stock solutions were individually prepared in acetonitrile except for betaine, which was prepared in water. Target stock concentrations were 500 μg/mL for all calibrant compounds, with the exception of HP-2121 and HP-2721. The former was prepared at 175 μg/mL and the latter, which exhibits lower solubility, was added neat to the acetonitrile solution and mixed thoroughly for two hours with the aid of an ultrasonic bath held at 40° C. TFA ammonium salt, betaine and water were added last, and the solution was mixed again.

TABLE 2

Electrospray Tuning Mix (one liter preparation)

| Compound | Final Solution Concentration | Monoisotopic Gram Molecular Weight | Stock Solution Concentration | Aliquot | Gravimetric Amount |
|---|---|---|---|---|---|
| TFA ammonium salt | 2.0 mM | 131.02 g/mole | neat | 0.2620 g | 0.2620 g |
| HP-0117 | 10 μM | 117.09 g/mole | 249.3 μg/ml | 4.697 ml | 1.171 mg |
| HP-0321 | 0.6 μM | 321.04 g/mole | 501.6 μg/ml | 0.384 ml | 9.193 mg |
| HP-0585 | 20 μM | 584.98 g/mole | 500.0 μg/ml | 23.399 ml | 11.700 mg |
| HP-0621 | 15 μM | 621.02 g/mole | 511.9 μg/ml | 18.198 ml | 9.316 mg |
| HP-0921 | 20 μM | 921.00 g/mole | 506.7 μg/ml | 36.353 ml | 18.420 mg |
| HP-1521 | 15 μM | 1520.96 g/mole | 433.7 μg/ml | 52.604 ml | 22.814 mg |
| HP-2121 | 22 μM | 2120.92 g/mole | 176.3 μg/ml | 264.664 ml | 46.660 mg |
| HP-2721 | 27 μM | 2720.88 g/mole | neat | 73.464 mg | 73.464 mg |

TABLE 2-continued

Electrospray Tuning Mix (one liter preparation)

| Compound | Final Solution Concentration | Monoisotopic Gram Molecular Weight | Stock Solution Concentration | Aliquot | Gravimetric Amount |
|---|---|---|---|---|---|
| ACN:H₂O | 95:5 by volume | | | | |

Figure 1:
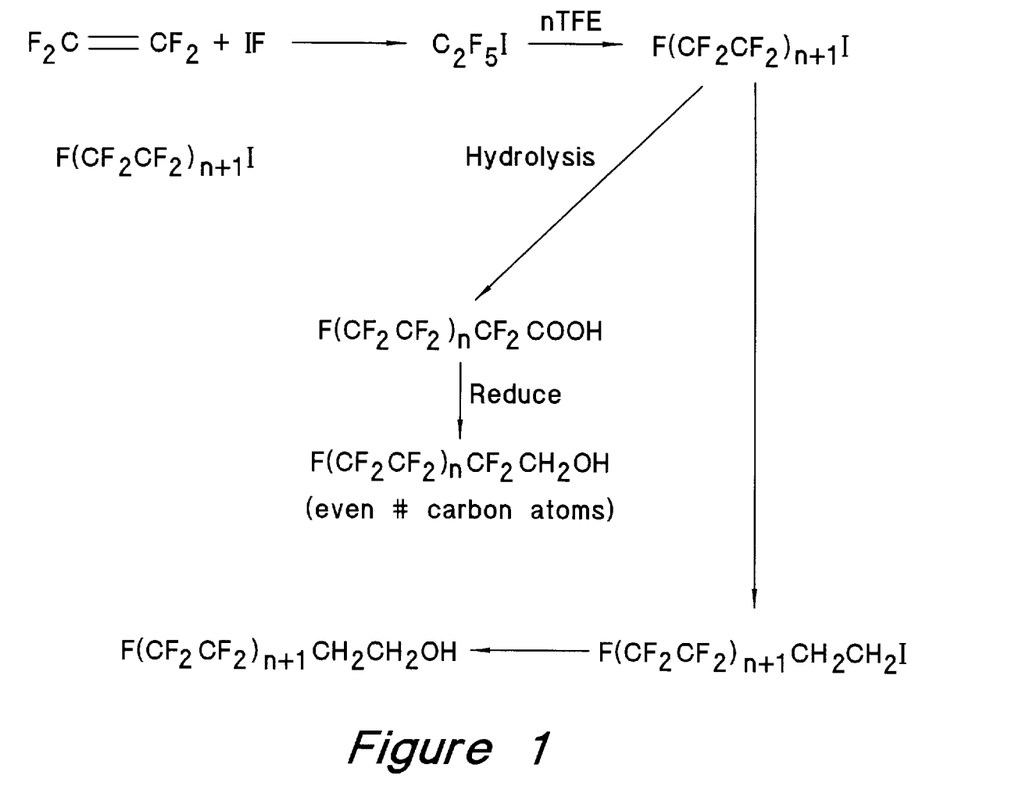
FIGS. 1 through 4 schematically illustrate the synthesis of homogeneously substituted triazatriphosphorines useful as the primary calibrants in the novel compositions.
Figure 2:
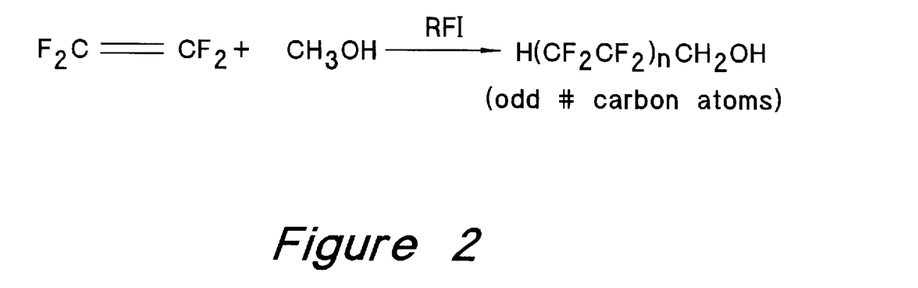
Figure 3:
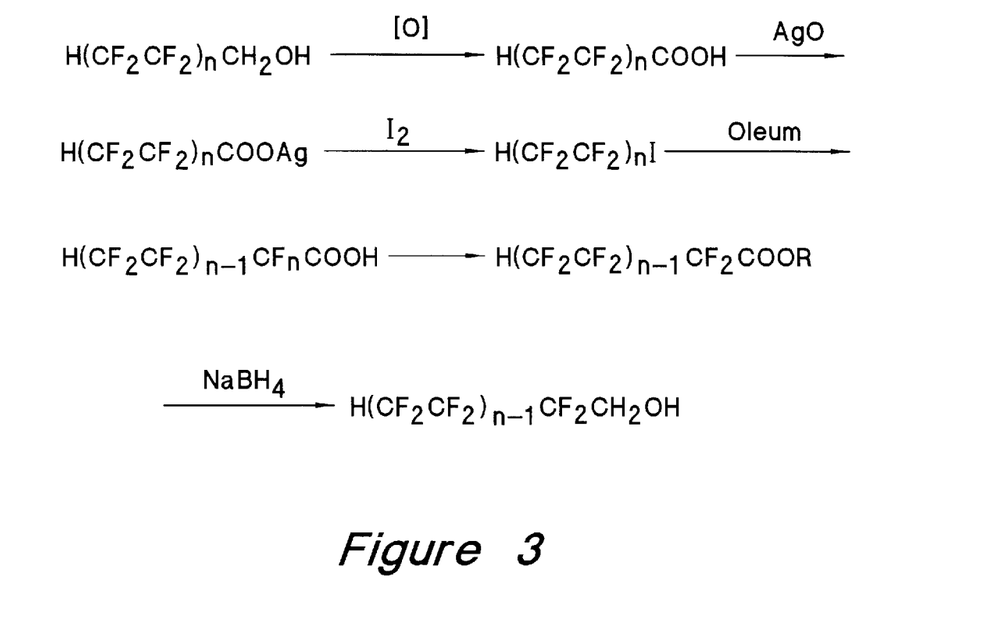
Figure 4:
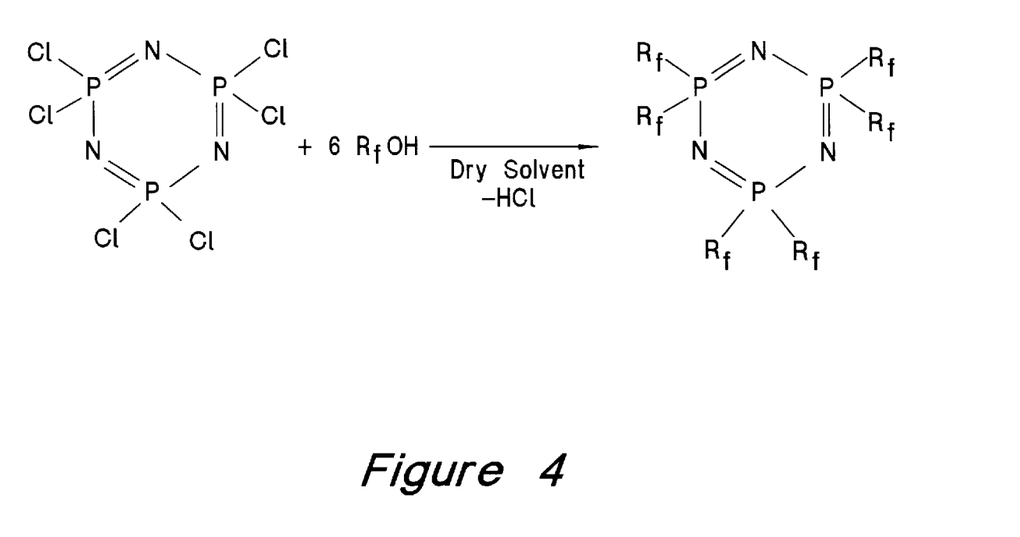
Figure 5:
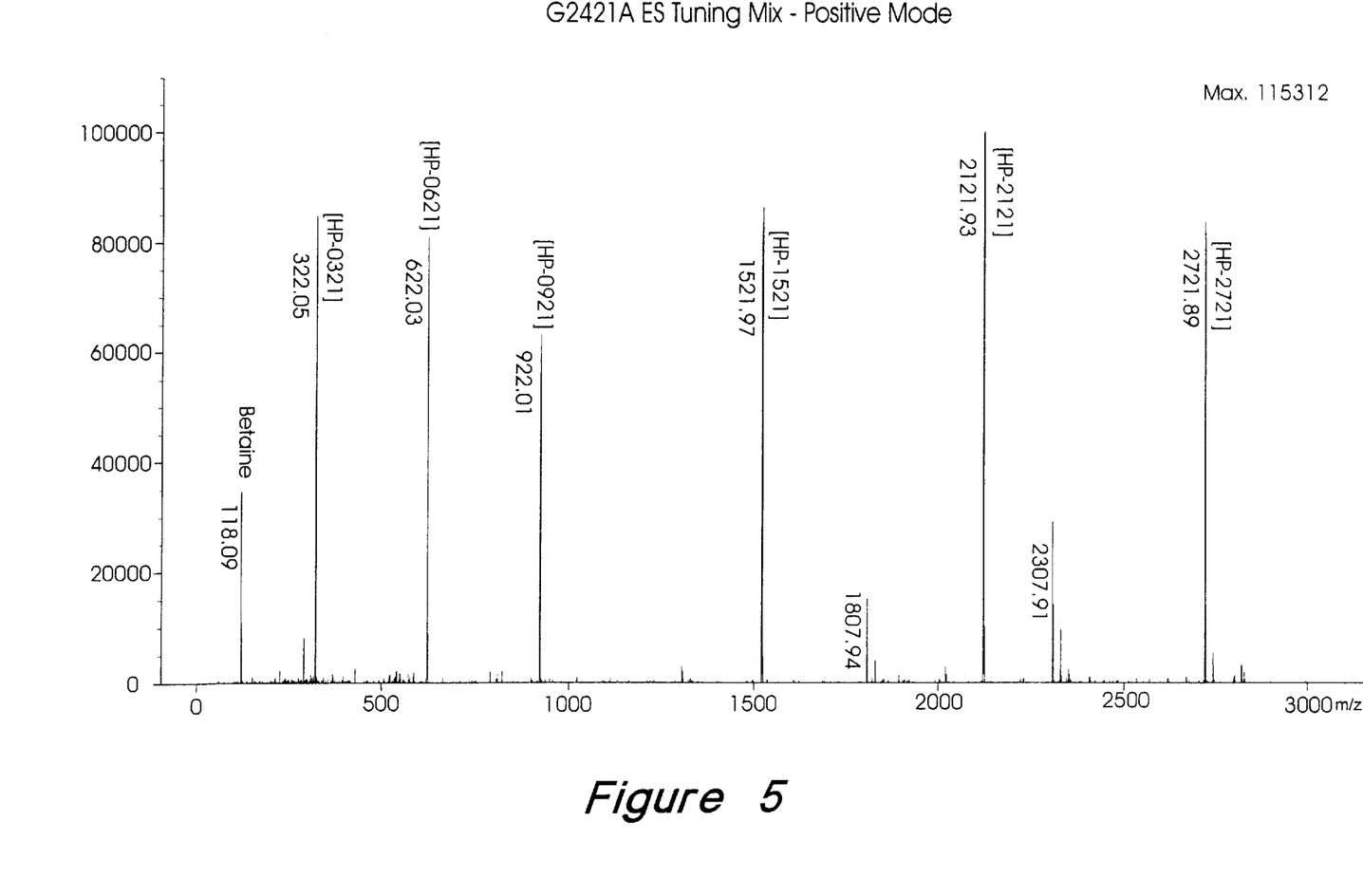
FIG. 5 is a mass spectrum of a calibrant composition of the invention obtained using a mass spectrometer with an API-electrospray ion source in positive-ionization mode.
Figure 6:
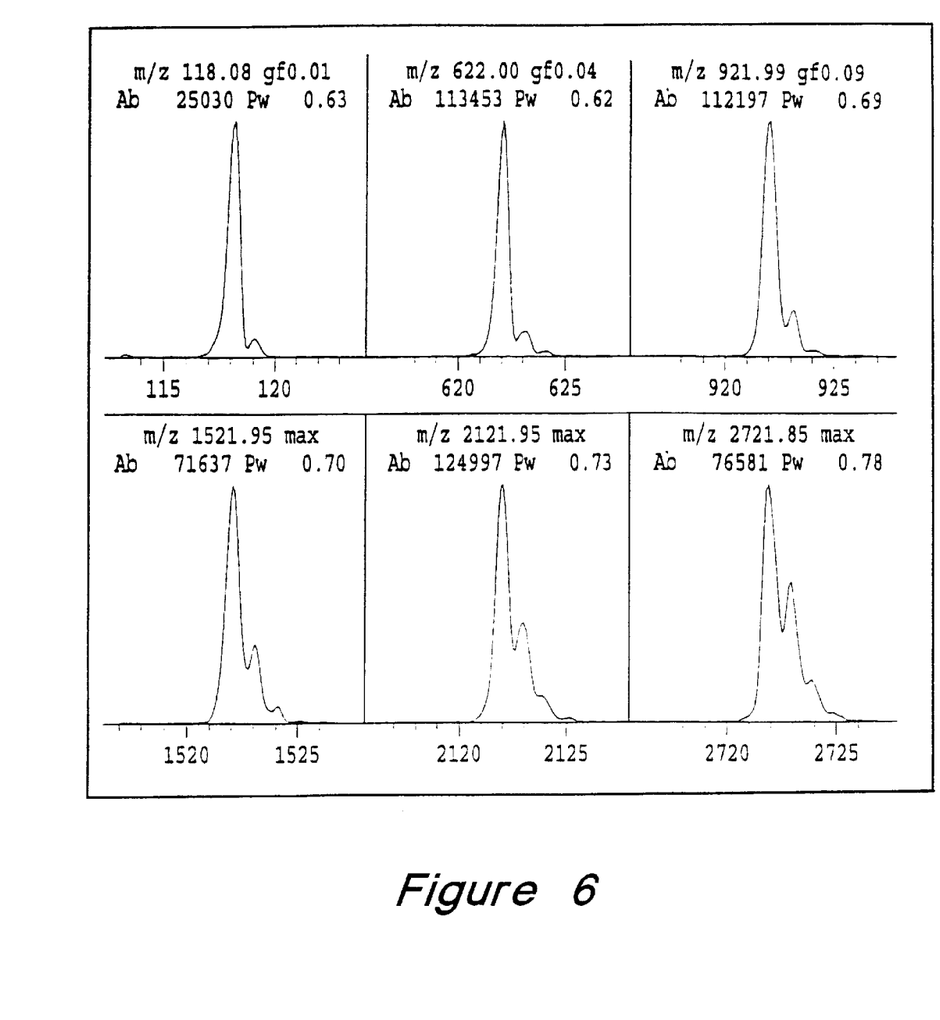
FIG. 6 shows mass peak profiles resulting from an API-ES positive ion mode tune.
Figure 7:
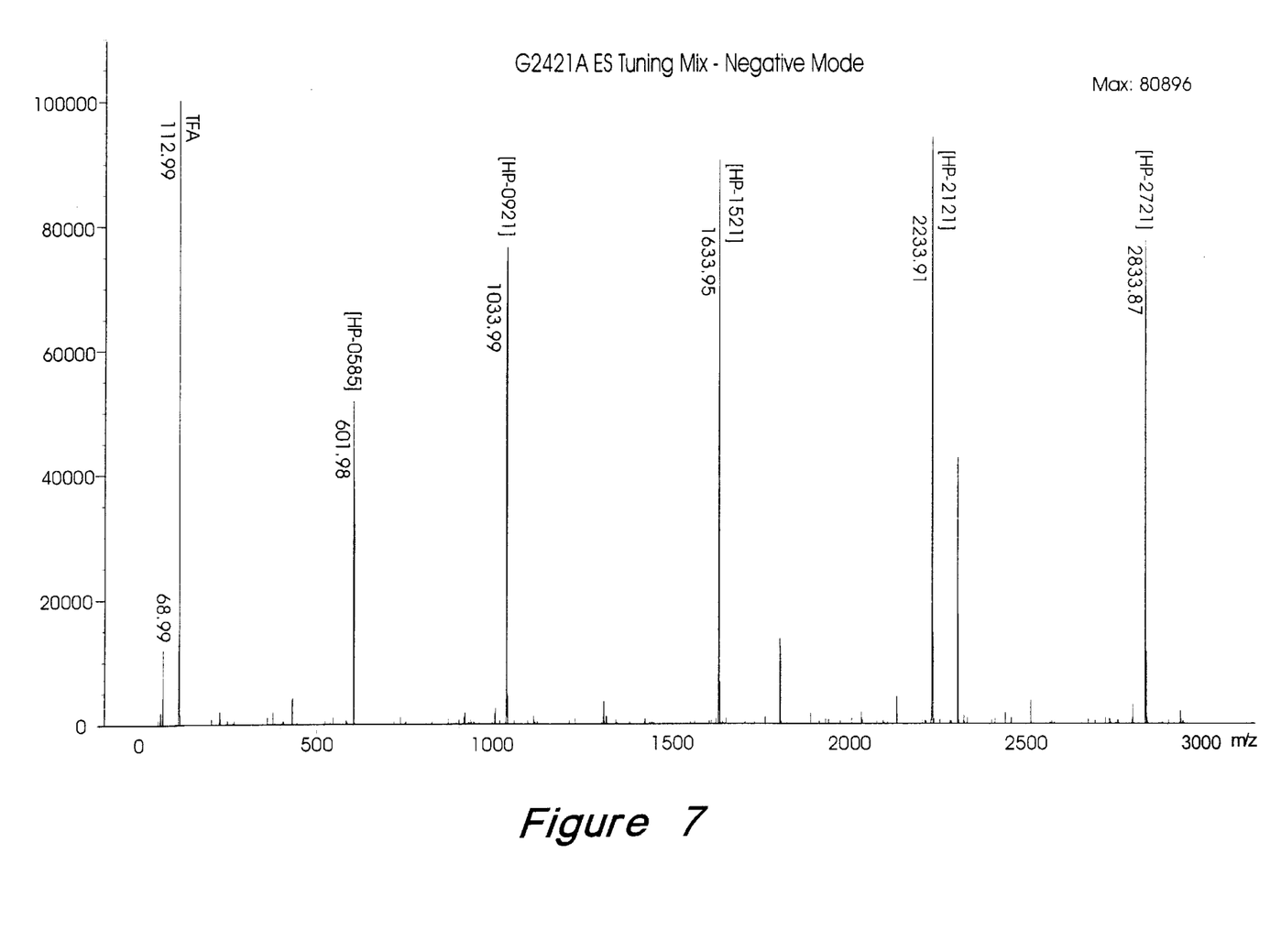
FIG. 7 is a mass spectrum of a calibrant composition of the invention obtained using a mass spectrometer with an API-electrospray ion source in negative-ionization mode.
Figure 8:
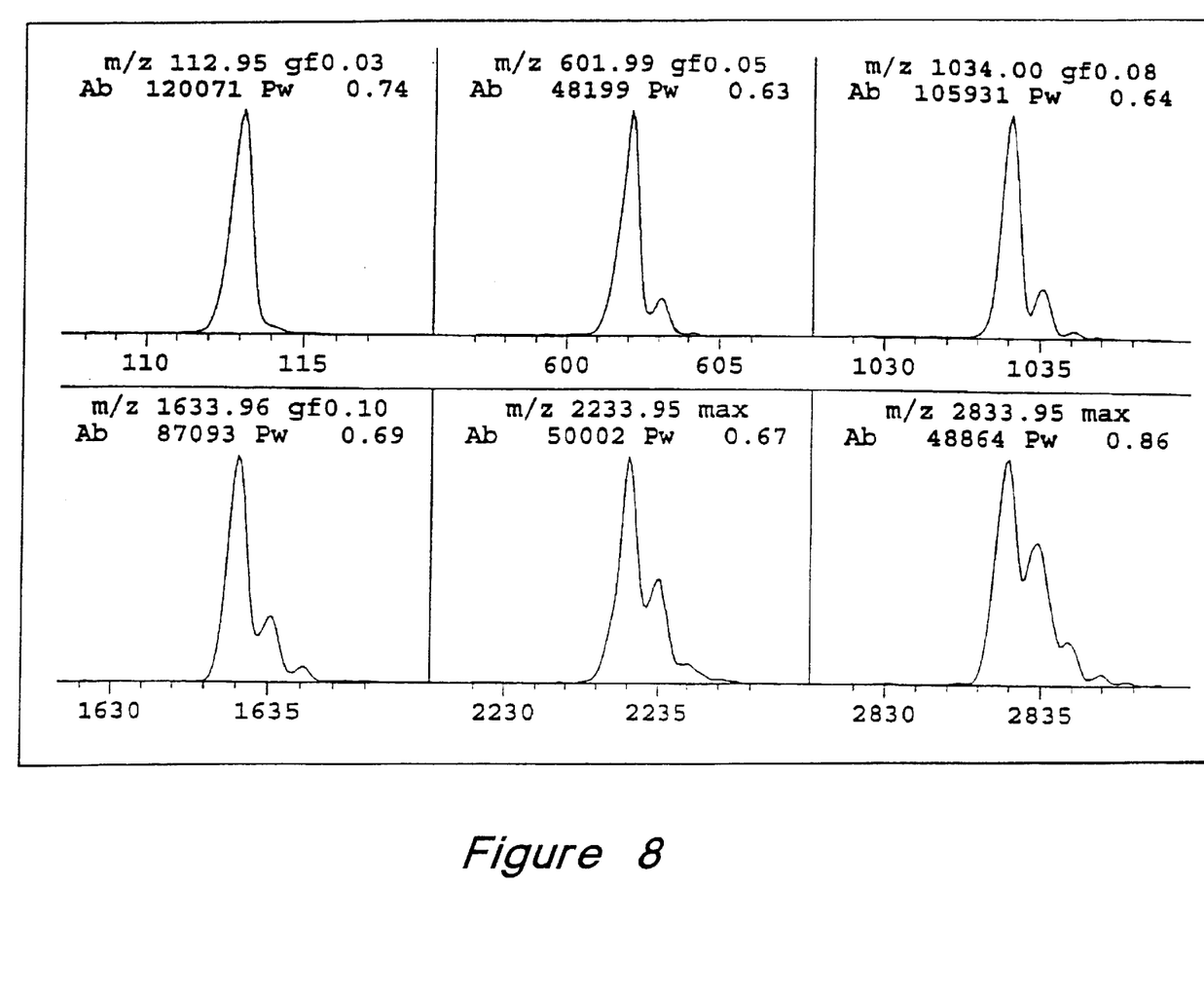
FIG. 8 shows mass peak profiles resulting from an API-ES negative ion mode tune.

Abbreviations:
TFA: trifluoroacetic acid
HP-0117: betaine
ACN: acetonitrile
HP-0585: Tris(heptafluoropropyl)-s-triazine FIG. 5 shows the mass spectrum of this calibrant composition obtained in electrospray positive-ionization mode. FIG. 6 show the mass peak profiles resulting from an API-ES positive ion mode tune. The mass spectrometer was then calibrated in electrospray negative-ionization mode, and the spectrum obtained is shown in FIG. 7. FIG. 8 shows the mass peak profiles resulting from an API-ES negative ion mode tune.

EXAMPLE 2

A composition for use in APCI mass spectrometry calibration was prepared containing the components set forth in Table 3.

TABLE 3

APCI Tuning Mix (one liter preparation)

| Compound | Final Solution Concentration | Monoisotopic Gram Molecular Weight | Stock Solution Concentration | Aliquot | Gravimetric Amount |
|---|---|---|---|---|---|
| HP-0120 | 50 μM | 120.04 g/mole | 504.0 μg/ml | 10.905 ml | 6.002 mg |
| HP-0321 | 5 μM | 321.04 g/mole | 501.6 μg/ml | 3.200 ml | 1.605 mg |
| HP-0621 | 10 μM | 621.02 g/mole | 511.9 μg/ml | 12.132 ml | 6.210 mg |
| HP-0921 | 12 μM | 921.00 g/mole | 506.7 μg/ml | 21.812 ml | 11.052 mg |
| HP-1521 | 10 μM | 1520.96 g/mole | 433.7 μg/ml | 35.069 ml | 15.209 mg |
| HP-2121 | 15 μM | 2120.92 g/mole | 176.3 μg/ml | 108.453 ml | 31.814 mg |

Figure 9:
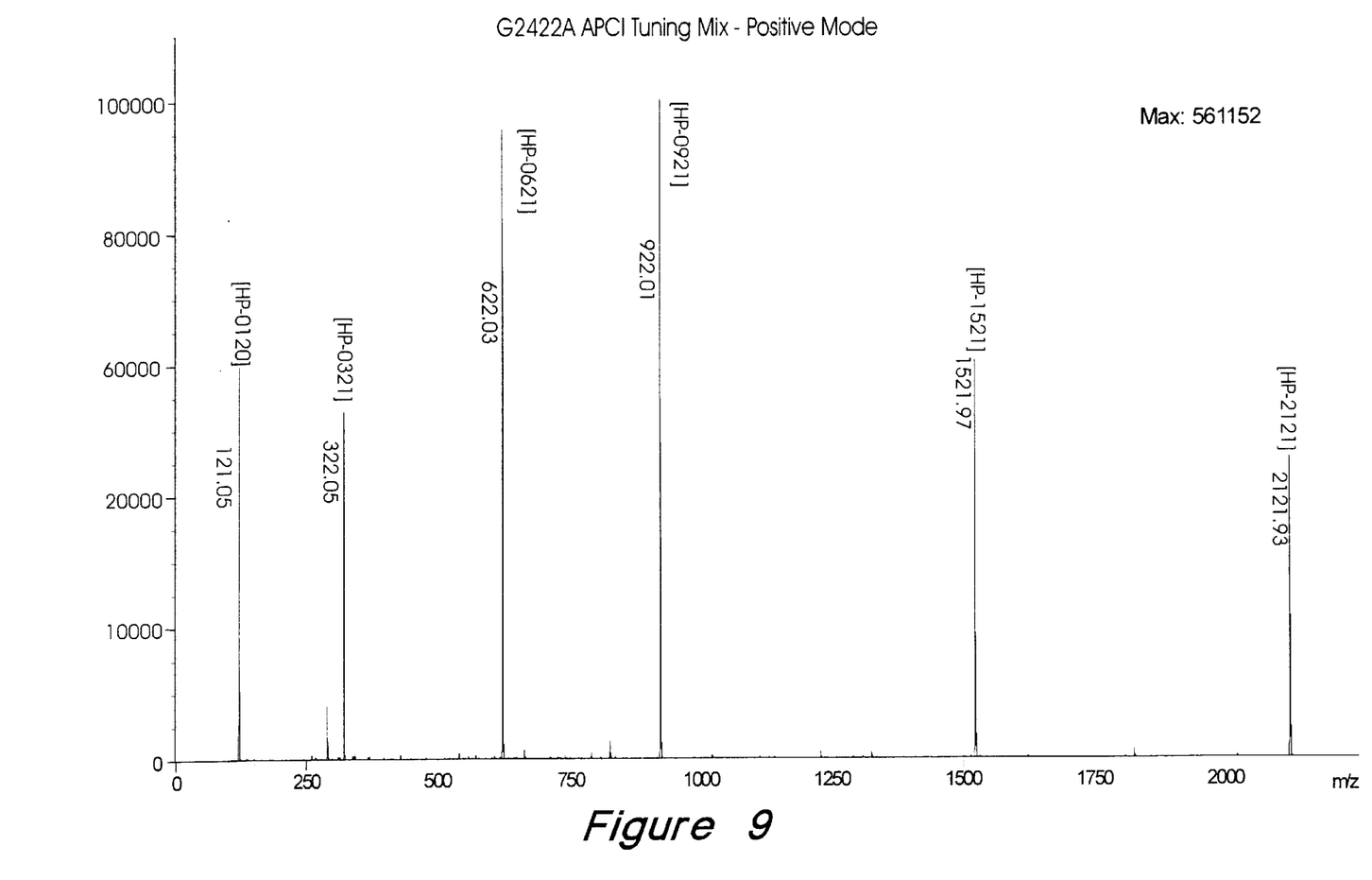
FIG. 9 is a mass spectrum of a calibrant composition of the invention obtained using a mass spectrometer with an APCI ion source in positive-ionization mode.
Figure 10:
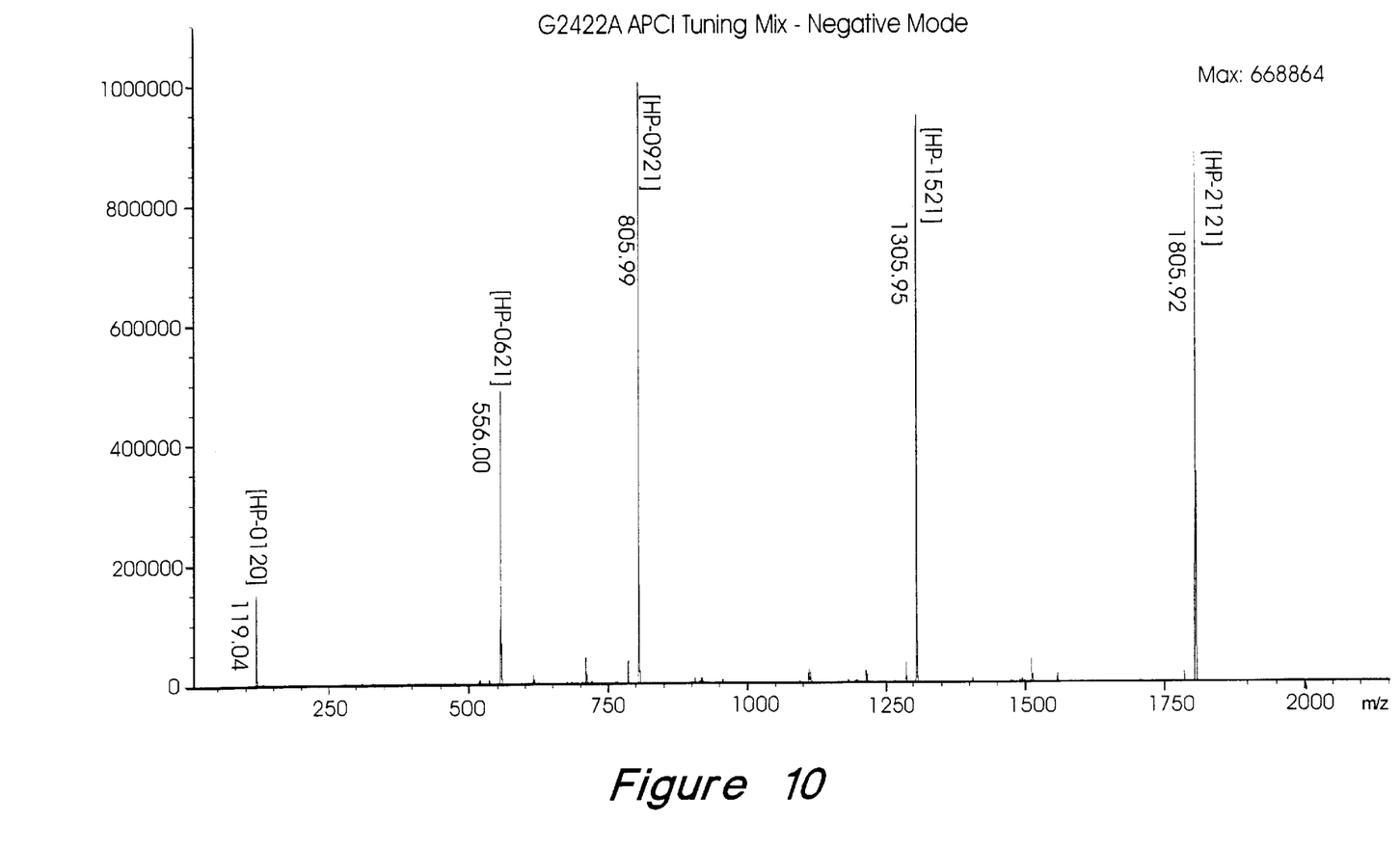
FIG. 10 is a mass spectrum of a calibrant composition of the invention obtained using a mass spectrometer with an APCI ion source in negative-ionization mode.

Solution prepared in 80:15:4:1 acetonitrile:methanol:water:chloroform.
Abbreviation:
HP-0120: purine FIG. 9 shows the mass spectrum of this calibrant composition obtained in APCI positive-ionization mode. The mass spectrometer was then calibrated in APCI negative-ionization mode, and the spectrum obtained is shown in FIG. 10.

The peaks in the spectra of FIGS. 5, 7, 9 and 10 are labeled with their corresponding monoisotopic mass-to-charge ratios; reference masses are as follows:

TABLE 4

REFERENCE MASSES FOR ES AND APCI

| Masses | Positive ES | Negative ES | Positive APCI | Negative APCI |
|---|---|---|---|---|
| Mass 1 | 118.10 | 112.99 | 121.05 | 119.04 |
| Mass 2 | 322.05 | (frag) 431.98 | 322.05 | N/A |

TABLE 4-continued

REFERENCE MASSES FOR ES AND APCI

| Masses | Positive ES | Negative ES | Positive APCI | Negative APCI |
|---|---|---|---|---|
| Mass 3 | 622.03 | 601.98 | 622.03 | 556.00 |
| Mass 4 | 922.01 | 1033.99 | 922.07 | 805.99 |
| Mass 5 | 1521.97 | 1633.95 | 1521.97 | 1305.95 |
| Mass 6 | 2121.93 | 2233.91 | 2121.93 | 1805.92 |
| Mass 7 | 2721.89 | 2833.87 | N/A | N/A |

The calibrant compositions of the invention may, accordingly, be used across a very broad range of m/z values, and provide reference mass peaks in both ion polarities (i.e., both positive and negative). In addition, substantially the same components can be used for both electrospray and APCI mass spectrometry.

EXAMPLE 4

Ten liters of a composition for use in electrospray mass spectrometer calibration may be prepared as follows:

| For a 10-liter ES preparation: | |
|---|---|
| Compound | Aliquot |
| TFA ammonium salt | 2.620 g |
| Betaine | 11.710 mg |
| HP-0321 | 1.926 mg |
| HP-0585 | 116.995 mg |

-continued

For a 10-liter ES preparation:

| Compound | Aliquot |
|---|---|
| HP-0621 | 93.156 mg |
| HP-0921 | 184.201 mg |
| HP-1521 | 228.144 mg |
| HP-2121 | 466.603 mg |
| HP-2721 | 734.638 mg |
| Solution prepared in acetonitrile:water, 95:5 by volume. | |

EXAMPLE 5

Ten liters of a composition for use in APCI mass spectrometer calibration may be prepared as follows:

For a 10-liter APCI preparation:

| Compound | Aliquot |
|---|---|
| HP-0120 | 60.020 mg |
| HP-0321 | 16.051 mg |
| HP-0621 | 62.104 mg |
| HP-0921 | 110.522 mg |
| HP-1521 | 152.094 mg |
| HP-2121 | 318.139 mg |
| Solution prepared in acetonitrile:methanol: water:chloroform, 80:15:4:1 by volume. | |

EXAMPLE 6

Figure 11:
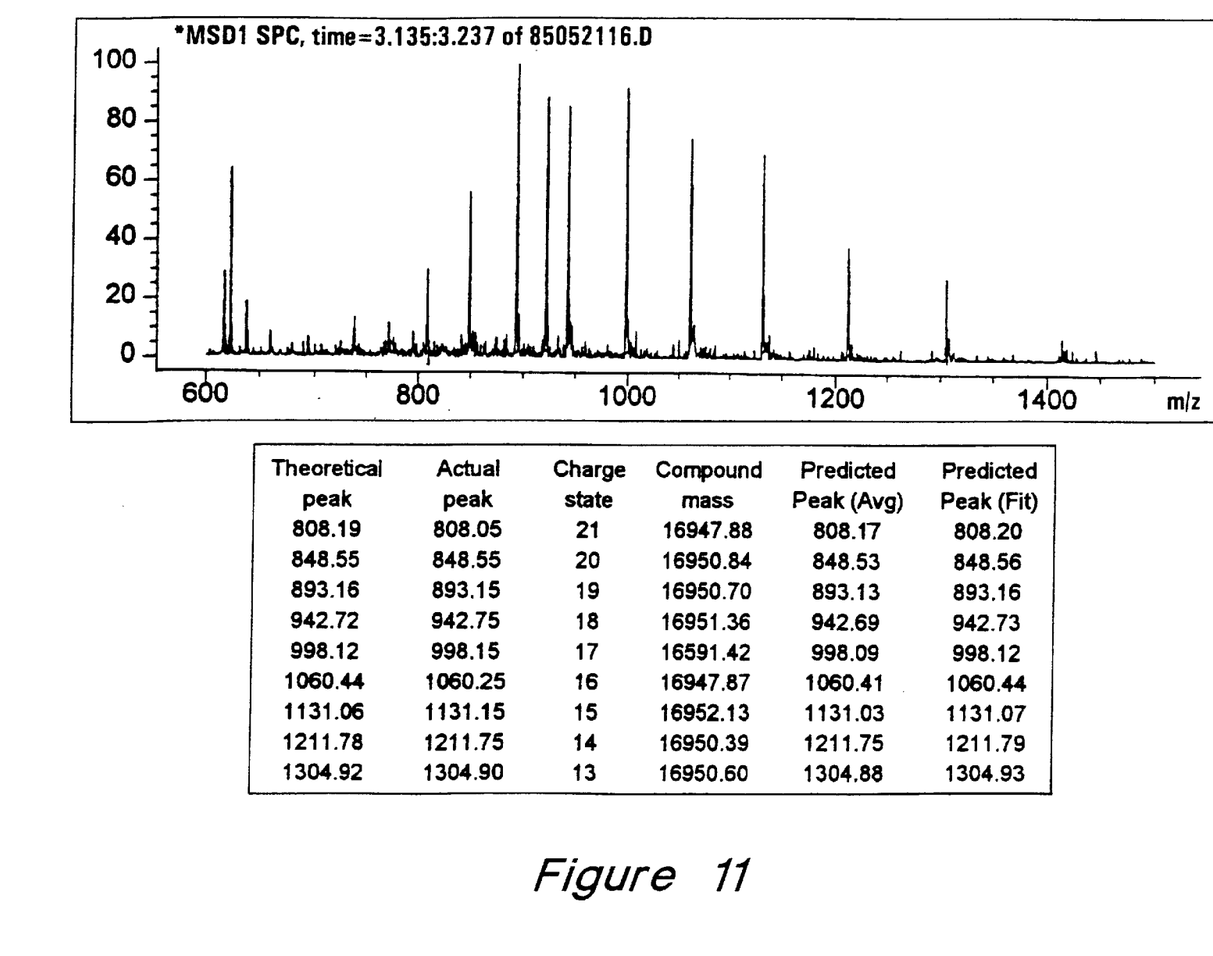
FIG. 11 shows the calibration conducted using a calibrant composition of the invention in conjunction with obtaining the electrospray mass spectrum of myoglobin.

Flow injection analysis (FIA) data was obtained for five injections of 15 pmole myoglobin (horse skeletal muscle) directly following an autotune calibration with the electrospray calibrant composition prepared in Example 4. The deconvolution result as well as the individual mass peaks representing different charge states of myoglobin were in excellent agreement with the reported value in the literature (16,950.97 Da); see FIG. 11.

LC/MS instrument conditions:

Instrument: HP 1100 series LC-MSD (Hewlett-Packard), product number G1946A with API-ES accessory (product number G1948A).

LC Flow Rate and Solvent Composition: 0.4 ml/min of 50:50 isopropanol:water with 1% acetic acid by volume.

Mode: Positive Ion API-Electrospray.

Mass Range Scanned: m/z 600–1500 at 0.1 amu stepsize.

Nominal Scan Rate: 500 amu/sec.

EXAMPLE 7

This example describes a representative synthesis of a fluorinated triazatriphosphorine as used in the present calibrant compositions.

Preparation of 2,2,4,4,6,6-hexahydro-2,2,4,4,6,6-hexakis ((2,2,3,3,4,4,5,5-octafluoropentyl)oxy)-1,3,5,2,4,6-triazatriphosphorine (HP-1521):

A 1-liter 3-necked round bottomed flask was fitted with a 250 mL addition funnel, a water-cooled reflux condenser with an argon (Ar) inlet, glass stopper, and magnetic stirring bar. This apparatus was flame-dried under dry Ar purge (the entire reaction sequence was run under an atmosphere of dry Ar).

7.27 g (0.303 mol) of dry NaH powder was then added directly to the flask, followed by 100 mL of dry THF (freshly distilled from sodium benzophenone ketyl). To this vigorously stirred suspension was added a solution of 63.88 g (0.275 mol) 1,1,5-tri-H-octafluoropentanol in 100 mL of dry THF. The rate of the dropwise, room-temperature addition was controlled such that the outside of the flask did not feel too warm to the touch (this addition is exothermic; the temperature of the reaction mixture should not exceed 45°–50° C.). When the addition was complete, the mixture was refluxed for two hours, and then allowed to cool to room temperature and stir overnight.

The following day, the addition funnel was charged with 14.5 g (0.0417 mol) of phosphonitrilic chloride trimer dissolved in 150 mL of dry tetrahydrofuran (THF). This was added dropwise to the reaction mixture at such a rate that the flask did not feel too warm to the touch (the temperature of the reaction mixture should not exceed 60° C). When the addition was complete, the mixture was refluxed for two hours, and then cooled to room temperature and allowed to stir overnight.

The following day, the THF was removed by rotary evaporation, and the resulting residue was treated with 250 mL water and 200 mL of diethyl ether. The phases were separated and the aqueous phase extracted 3 times with 100 mL of ether. The combined ether phases were then washed three times with 100 mL of water. The ethereal solution was then dried over anhydrous $MgSO_4$, rotary evaporated, and the residue was fractionally distilled under high vacuum to yield 51.7 g (82.6%) of hexa(1,1,5-tri-H-octafluoropentoxy) triphosphonitrile (2,2,4,4,6,6-hexahydro-2,2,4,4,6,6-hexakis ((2,2,3,3,4,4,5,5-octafluoropentyl)oxy)-1,3,5,2,4,6-triazatriphosphorine. b.p. 203°–207° C./0.25 mm Hg) as a colorless liquid. The identity of the product was confirmed using $^1H$ and $^{19}F$ NMR Spectroscopy.

EXAMPLE 8

This example describes a representative synthesis of an alternative fluorinated triazatriphosphorine as used in the present calibrant compositions.

Preparation of 2,2,4,4,6,6-hexahydro-2,2,4,4,6,6-hexakis ((2,2,3,3,4,4,5,5,6,6,7,7,8,8,8-pentadecafluorooctyl)oxy)-1,3,5,2,4,6-triazatriphosphorine (HP-2529):

A 1-liter 3-necked round bottomed flask was fitted with a 250 mL addition funnel, water-cooled reflux condenser with dry $N_2$ inlet, a thermometer, and magnetic stirring bar. This apparatus was flame-dried under dry $N_2$ purge (the entire reaction sequence is run under an atmosphere of dry $N_2$.

0.78g (32.5 mmol) of dry NaH powder was then added directly to the flask, followed by 100 mL of dry THF (freshly distilled from sodium benzophenone ketyl). To this vigorously stirred suspension was added a solution of 10.39 g of 97% Freon® 338 (1H,1H-perfluorooctanol) (25.2 mmol) in 180 mL of dry THF. The rate of the dropwise, room-temperature addition was controlled such that the temperature of the reactant mixture never exceeded 45° C. When the addition was complete, the mixture was refluxed for two hours, then allowed to cool to room temperature and stir overnight.

The following day, the addition funnel was charged with 1.40 g (4.0 mmol) of phosphonitrilic chloride trimer dissolved in 70 mL of dry THF. This was added dropwise to the reaction mixture at such a rate that the temperature of the reactant mixture did not exceed 50° C. When the addition was complete, the mixture was refluxed for two hours, then cooled to room temperature and allowed to stir overnight.

The following day, the THF was removed by rotary evaporation, and the resulting residue was treated with 250 mL water and 200 mL of Freon® 338. The phases were separated and the aqueous phase extracted 3 times with 100 mL of Freon®. The combined Freon® phases were then washed three times with 100 mL of water. The Freon® solution was then dried over anhydrous MgSO$_4$, rotary evaporated, and the resultant white solid was washed with hexanes to yield 9.84 g (96.7% yield) of hexa(1H,1H-perfluoroctyloxy)triphosphonitrile (2,2,4,4,6,6-hexahydro-2,2,4,4,6,6-hexakis ((2,2,3,3,4,4,5,5,6,6,7,7,8,8,8-pentadecafluorooctyl)oxy)-1,3,5,2,4,6-triazatriphosphorine) as a white solid. The product was finally dried under vacuum.

I claim:

1. A calibrating composition for use in mass spectrometry, comprising:
   a predetermined concentration of a primary calibrant comprised of a homogeneously substituted triazatriphosphorine compound;
   a predetermined concentration of a secondary calibrant comprised of a compound selected to enable calibration at an m/z below approximately 150; and
   a solvent effective to dissolve both the primary and secondary calibrants,
   wherein the primary and secondary calibrants can be used in either positive-ionization mode or negative-ionization mode.

2. The composition of claim 1, wherein the triazatriphosphorine compound has the structural formula (I)

(I)

wherein the R$_f$ substituents are identical and are selected from the group consisting of —OCH$_3$, —O—(CF$_2$)$_{n'}$—CF$_2$H, —O—(CH$_2$)$_m$—(CF$_2$)$_n$—CF$_2$R and —O—(CH$_2$)$_m$—(CF$_2$)$_{n-1}$—CHF—CF$_2$R in which m is 0, 1 or 2, n' is an integer in the range of 0 to 16, n is an integer in the range of 1 to 16 inclusive, and R is hydrogen or fluoro.

3. The composition of claim 2, wherein R is hydrogen.

4. The composition of claim 3, wherein m is 0, and n' is an integer in the range of 0 to 9 inclusive, and n is an integer in the range of 1 to 9 inclusive.

5. The composition of claim 2, wherein R is fluoro.

6. The composition of claim 2, wherein m is 1.

7. The composition of claim 2, wherein m is 0.

8. The composition of claim 2, comprising a plurality of different triazatriphosphorine compounds each having the structural formula (I), selected to enable calibration across a predetermined range of approximately 50 to 3000 m/z.

9. The composition of claim 8, comprising five to eight different triazatriphosphorine compounds each having the structural formula (I).

10. The composition of claim 8, comprising triazatriphosphorine compounds selected from the group consisting of:
2,2,4,4,6,6-hexahydro-2,2,4,4,6,6-hexamethoxy-1,3,5,2,4,6-triazatriphosphorine;
2,4,4,6,6-hexakis(2,2-difluoroethoxy)-2,2,4,4,6,6-hexahydro-1,3,5,2,4,6-triazatriphosphorine;
2,2,4,4,6,6-hexahydro-2,2,4,4,6,6-hexakis((2,2,3,3-tetrafluoropropoxy)-1,3,5,2,4,6-triazatriphosphorine;
2,2,4,4,6,6-hexakis((2,2,3,3,4,4,5,5,6,6,7,7-dodecafluoroheptyl)oxy)-2,2,4,4,6,6-hexahydro-1,3,5,2,4,6-triazatriphosphorine; and
2,2,4,4,6,6-hexakis((2,2,3,3,4,4,5,5,6,6,7,7,8,8,9,9-hexadecafluorononyl)-2,2,4,4,6,6-hexahydro-1,3,5,2,4,6-triazatriphosphorine.

11. The composition of claim 1, wherein the secondary calibrant is selected so as to enable calibration at an m/z below approximately 120.

12. The composition of claim 11, wherein the secondary calibrant is selected from the group consisting of betaine, purine and nitrogen-containing heterocycles substituted with a hydroxyl or carboxyl substituent.

13. The composition of claim 12, wherein the secondary calibrant is betaine.

14. The composition of claim 12, wherein the secondary calibrant is purine.

15. The composition of claim 12, wherein the secondary calibrant is a nitrogen-containing heterocycle substituted with a hydroxyl or carboxyl substituent.

16. The composition of claim 15, wherein the nitrogen-containing heterocycle is an amphoteric compound selected from the group consisting of 3-hydroxy-2-ethylpyridine, 2-hydroxypyridine, 3-hydroxypyridine and picolinic acid.

17. The composition of claim 1, further including a fluorinated triazine, and wherein the composition is useful in calibrating an electrospray mass spectrometer.

18. The composition of claim 17, wherein the fluorinated triazine has the structural formula (II)

(II)

wherein each R' is —(CF$_2$)$_p$CF$_3$ wherein p is an integer in the range of 1 to 8 inclusive.

19. The composition of claim 17, wherein the fluorinated triazine is tris(heptafluoropropyl)-1,3,5-triazine.

20. The composition of claim 17, further including a compound selected from the group consisting of $C_2$–$C_{18}$ fluorinated acids and salts thereof.

21. The composition of claim 20, wherein the compound is a salt of a $C_2$–$C_{10}$ fluorinated acid.

22. The composition of claim 20, wherein the compound is the ammonium salt of trifluoroacetic acid.

23. The composition of claim 1, wherein the solvent contains substantially no free acid.

24. The composition of claim 23, wherein the solvent is comprised of a mixture of acetonitrile and water.

25. The composition of claim 24, comprising up to about 5 vol. % water.

26. The composition of claim 1, wherein the triazatriphosphorine compound has the structural formula (Ia)

(Ia)

wherein the R'$_f$ within any one compound are identical, and are selected from the group consisting of:
—OCH$_2$(CF$_2$)$_2$CF$_2$H;    —OCH$_2$(CF$_2$)$_4$CF$_2$H;
—OCH$_2$(CF$_2$)$_6$CF$_2$H;    —OCH$_2$(CF$_2$)$_8$CF$_2$H;
—OCH$_2$(CF$_2$)$_6$CF$_3$;  —OCH$_2$(CF$_2$)$_8$CF$_3$;  and  —OCH$_2$—CF$_2$—CFH—CF$_3$.

27. The compound of claim 26, wherein R'$_f$ is —OCH$_2$(CF$_2$)$_2$CF$_2$H.

28. The compound of claim 26, wherein R'$_f$ is —OCH$_2$(CF$_2$)$_4$CF$_2$H.

29. The compound of claim 26, wherein R'$_f$ is —OCH$_2$(CF$_2$)$_6$CF$_2$H.

30. The compound of claim 26, wherein $R'_f$ is —$OCH_2(CF_2)_8CF_2H$.

31. The compound of claim 26, wherein $R'_f$ is —$OCH_2$—$CF_2$—$CHF$—$CF_3$.

32. In a method for calibrating a mass spectrometer, comprising obtaining a mass spectrum of a calibrant composition containing a plurality of known compounds, determining the differences between the expected mass peaks for each of the known compounds and the corresponding actual mass peak obtained, and, based on those differences, adjusting the mass spectrometer, the improvement comprising using a calibrant composition comprising:

(a) a predetermined concentration of a primary calibrant comprised of a homogeneously substituted triazatriphosphorine compound;

(b) a predetermined concentration of a secondary calibrant comprised of a compound selected to enable calibration at an m/z below approximately 150; and (c) a solvent effective to dissolve both the primary and secondary calibrants, wherein the primary and secondary calibrants can be used in either positive-ionization mode or negative-ionization mode.

* * * * *